United States Patent [19]

Bernstein

[11] Patent Number: 4,541,800
[45] Date of Patent: Sep. 17, 1985

[54] DENTAL APPLIANCE HAVING ENHANCED OCCLUSAL DURABILITY

[76] Inventor: Ira M. Bernstein, 14 Burlington Ave., Suffern, N.Y. 10901

[21] Appl. No.: 566,202

[22] Filed: Dec. 28, 1983

[51] Int. Cl.⁴ ............................................. A61C 3/00
[52] U.S. Cl. ...................................................... 433/6
[58] Field of Search ................. 433/6, 1, 225; 128/136

[56] References Cited

U.S. PATENT DOCUMENTS

| | | | |
|---|---|---|---|
| 2,438,725 | 3/1948 | Tamarin | 433/225 |
| 3,462,838 | 8/1969 | Alstergren | 433/1 |
| 3,510,946 | 5/1970 | Kesling | 433/6 |
| 4,330,272 | 5/1982 | Bergersen | 433/6 |
| 4,396,373 | 8/1983 | Dellinger | 433/6 |

Primary Examiner—John J. Wilson
Attorney, Agent, or Firm—Michael E. Zall

[57] ABSTRACT

This invention is directed to a method of enhancing the occlusal durability of a dental appliance and the dental appliance produced by such method. The method comprises embedding in the appliance at an occlusal contact area a wear resistant occlusal plug having a means thereon for anchoring the plug in the appliance. The method is particularly useful for enhancing the occlusal durability of a mandibular orthopedic repositioning appliance (MORA).

19 Claims, 4 Drawing Figures

DENTAL APPLIANCE HAVING ENHANCED OCCLUSAL DURABILITY

BACKGROUND OF THE INVENTION

1. Field of the Invention

This invention relates to a dental appliance, and particularly relates to an improved temporomandibular joint appliance, specifically a mandibular orthopedic repositioning appliance (MORA).

2. Prior Art

Acrylic resin temporomandibular joint appliances, such as mandibular orthopedic repositioning appliances (MORA), and their method of manufacture are well known in the art, see for example Gelb, Effective Management and Treatment of the Craniomandibular Syndrome, "Clinical Management of Head, Neck and TMJ Pain and Dysfunction", H. Gelb, ed. Phila., W. B. Saunders Co., 1977; and Lader, "TMJ: Clinical and Practice Management", 1981 by Vadare, Inc. Wantagh, N.Y. One of the main advantages of a mandibular orthopedic repositioning appliance, hereinafter MORA, is the ease with which the appliance can be adjusted to the patient. The material from which it is made, usually a self curing acrylic, can be easily reduced with a handpiece or built up with the acrylic as a chairside procedure.

Typically, after a patients symptoms have been satisfactorily reduced, the patient will undergo one of several other treatments to better stabilize the jaw position, e.g. crown and bridge reconstruction, functional orthodontics, overlay partial dentures or a combination of any of these procedures, see Gelb et al, "Clinical Evaluation of Two Hundred Private Practice Patients with TMJ Syndrome", J. Prosthet. Dent. 1983 Feb. 49:237. Unfortunately, these other type treatments may be unacceptable or impractical for some patients due to financial or time constraints. In these cases a solution is for the patient to wear a MORA as it has been constructed. However, the properties of the material, from which the MORA is constructed, e.g. acrylic, which makes it desirable during the treatment and construction stage, become a disadvantage. The MORA when worn by the patient for an extended period of time can chip, distort and wear down causing a subsequent decrease in the vertical dimension of the MORA. This in turn changes the position of the condyles and their fossae which may bring about the reoccurance of some or all of the patients symptoms.

In the past, amalgam stops have been placed in the acrylic at the points or areas of occlusal contact. These amalgam stops may slow the wearing down process, but for a patient who bruxes persistently they are inadequate, for they rapidly wear down and/or come loose. The wearing down of the occlusal surface of a dental appliance is not only common to MORAS but other type dental appliances, e.g. shore auto-repositioning appliance, myocentric appliance, dentures, etc.

OBJECTS AND SUMMARY OF THE INVENTION

It is an object of this invention to provide an improved dental appliance having enhanced occlusal durability.

It is a further object of this invention to provide a temporomandibular joint appliance, e.g. a mandibular orthopedic repositioning appliance (MORA) having enhanced occlusal durability.

It is still a further object of this invention to provide an occlusal plug for embedding in a dental appliance to enhance the occlusal durability of said appliance.

It is another object of this invention to provide a method of embedding such occlusal plug in a polymeric dental appliance.

It is still another object of this invention to provide an inexpensive method for preventing wear of the acrylic in a mandibular orthopedic repositioning appliance.

All of the foregoing objects of the invention, as well as others, are achieved by an improved dental appliance and a method for enhancing the occlusal durability of said dental appliance. The method comprises embedding in the appliance at an occlusal contact area a wear resistant occlusal plug having a means thereon for anchoring the plug in the appliance. The method is particularly useful for enhancing the occlusal durability of a mandibular orthopedic repositioning appliance (MORA).

BRIEF DESCRIPTION OF THE DRAWINGS

The invention will be more readily understood by reference to the accompanying drawings in which.

DETAILED DESCRIPTION OF THE INVENTION

Figure 1:
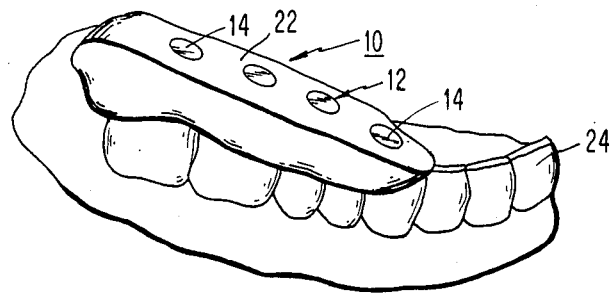
FIG. 1 is a perspective view of the improved dental appliance, e.g. MORA, of this invention in use.
Figure 2:
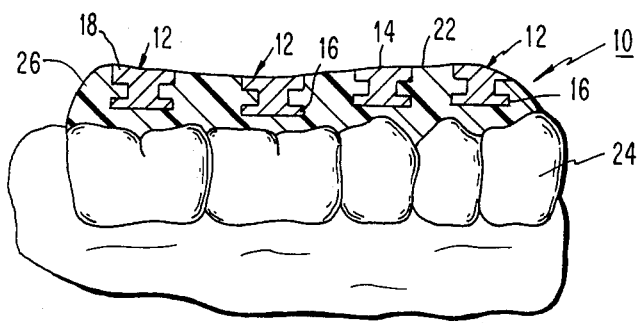
FIG. 2 is a cross-sectional view of the MORA of FIG. 1.

Referring to FIGS. 1 through 4, this invention is directed to an improved dental appliance, generally designated 10, and as depicted in the Figures herein an improved temporomandibular joint appliance, specifically a mandibular orthopedic repositioning appliance (MORA). It should be realized that the invention described herein may be applicable to other type dental appliances, e.g. jaw repositioning devices, dentures, shore auto repositioning appliance, myocentric splint, etc.

The invention comprises embedding in the MORA 10, a wear resistant occlusal plug, generally designated 12 which is embedded in the appliance at an occlusal contact area or point 14. The plug 12, which for ease of manufacture is cylindrical, has a means thereon, generally designated 16 for anchoring the plug 12 in the appliance 10. These plugs 12, are embedded in the acrylic 26 of the MORA 10 to forstall occlusal wear.

Figure 3:
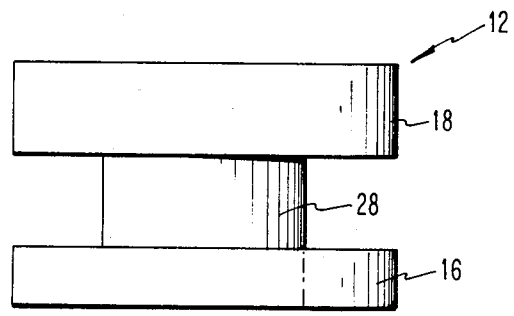
FIG. 3 is a side view of the occlusal plug used in this invention.
Figure 4:
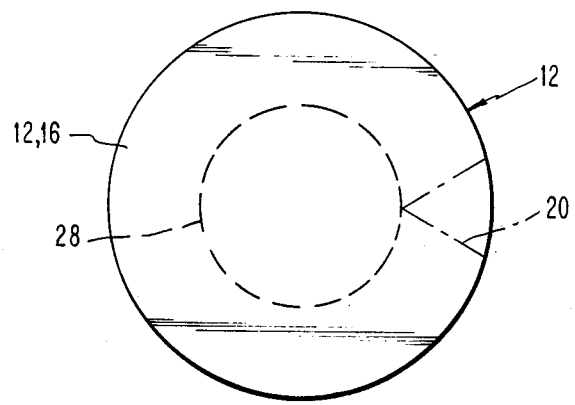
FIG. 4 is a top view of the occlusal plug of FIG. 3.

In the preferred embodiment depicted in FIGS. 3 and 4, the occlusal plug 12 is dumbbell shaped with one end 16 serving as an anchoring means and the other end 18 serving as the occlusal contact area. The plug 12 is embedded in the acrylic 26 with the acrylic filling in around the narrow member 28 above the anchoring end 16 and below end 18 serving as the occlusal contact area. Thus it is difficult, if not impossible, for the plug 12 to be unintentionally removed from the MORA or, for that matter, for the plug 12 to sink substantially below the initial seating position.

In the embodiment depicted in FIGS. 3 and 4, the end of plug 12 which serves as the anchoring means, i.e. 16, has a securing means, i.e. notch 20, formed therein to prevent rotation of the plug 12 when the notch 20 is filled with acrylic. Preferably, the plugs 12 are cast of a wear resistant non-precious metal. Preferably, although not necessarily, the occlusal plug contact area 18 is harder than the occlusal surface 22 of the dental appliance and softer than the teeth which come in contact with the occlusal surface 22.

The occlusal plug 12 may be made in various sizes. Generally it has been found that a large molar size and a small premolar size are adequate for most treatments. However, these are interchangable and may be placed as the available space in the appliance dictates. Typical dimensions for a plug 12 are from 2 to 4 mm in diameter and 2 mm in height. The number of plugs utilized in a MORA may vary from patient to patient.

If necessary an occlusal plug may be removed from a dental appliance and be reseated and/or it can be salvaged from an old dental appliance, air-abraded, polished, sterilized, and used again in another dental appliance.

The MORA 10, before embedding occlusal plugs 12 therein, should be perfectly balanced using the technique described in the aformentioned Gelb reference. Adjustments after embedding and seating the occlusal plug in the MORA should be kept to a minimum due to the fact that the metal plugs are extremely hard and difficult to grind.

The occlusal plugs are embedded in the polymer, e.g. acrylic, dental appliance as follows:

(a) Occlusal contact points or areas are located on the occlusal surface with articulating paper.
(b) An opening is prepared at the occlusal contact area using any suitable bur. The plugs are positioned one at a time on each side of the MORA. This provides the patient with several definite stops on each side of the MORA to guide the jaw into proper position while closing down on an occlusal plug. The preparation of the opening must be deep enough for the occlusal plug to seat fully below the occlusal plane.
(c) A mix of acrylic resin is next flowed into each opening. The acrylic is allowed to become slightly doughy in consistency. The occlusal plugs are then placed into position. The plugs should not be fully seated into the acrylic.
(d) The MORA is then placed in the patients mouth. The patient should gently close his mouth making sure that there is full contact on all portions of the appliance so that the occlusal plugs are seated to the existing occlusal plane.
(e) The acrylic is then allowed to harden and/or is cured, and any flash acrylic is removed.
(f) The procedure is then repeated again with two other occlusal plugs one on each side of the MORA. The foregoing steps are continued until all occlusal plugs are inserted in place.

Fine occlusal equilibration may then be indicated and performed, and the appliance polished with rubber wheel and pumice.

The improved dental appliance and method described and claimed herein can be completed in one visit to a dental office. It is a method which can prolong mandibular stabilization when time or financial limitations make other types of treatment impractical. The plugs prevent the decrease in vertical dimension of the MORA and changes in condylar position that are most likely to bring on a recurrence of symptons. However, when the improved MORA of this invention is used for an extended period of time adjustments may be necessary requiring periodic maintenance appointments to check and/or adjust the balance and fit.

The technique described herein in addition to its use in long term MORA therapy, can be used as a "holding pattern" before more definitive procedures are begun. The technique described heerein may also have application in the modification of removable partial dentures or full dentures when bruxism is a problem, in the fabrication of overlay removable partial dentures for TMJ disorder patients, etc.

From the foregoing, it is clear that the invention provided hwerein provides a method of enhancing the occlusal durability of a dental appliance. It is recognized of course, the those skilled in the art may make various modifications or additions to the embodiments chosen to illustrate the invention without departing from the gist and essence of the present contribution of the art. According, it is to be understood that the protection sought and to be afforded hereby should be deemed to extend to the subject matter claimed and all equivalents thereof falling within the scope of the invention.

What is claimed is:

1. A method of enhancing the occlusal durability of a dental appliance having an occlusal surface thereon comprising embedding in the appliance through an occulsal contact area a preformed wear resistant cylindrical dumbbell shaped occlusal plug, one end of the plug serving as a means for anchoring the plug in the appliance, and the other end of the plug serving as the occlusal contact area.

2. A method of enhancing the occlusal durability of a temporomandibular joint appliance having an occlusal surface thereon comprising embedding in the appliance through an occlusal contact area a preformed wear resistant cylindrical dumbbell shaped occlusal plug, one end of the plug serving as a means for anchoring the plug in the appliance, and the other end of the plug serving as the occlusal contact area.

3. A method of enhancing the occlusal durability of a mandibular orthopedic repositioning appliance having an occlusal surface thereon comprising embedding in the appliance through an occlusal contact area a preformed wear resistant cylindrical dumbbell shaped plug, one end of the plug serving as a means for anchoring the plug in the appliance, and the other end of the plug serving as the occlusal contact area.

4. The method of claim 3 wherein a major portion of the appliance is made of an acrylic resin in which the occlusal plug is embedded.

5. The method of claim 3, wherein the one end of the plug serving as the anchoring end has a securing means for preventing rotation of the plug.

6. The method of claim 5, wherein the securing means is a notch in the anchoring end of the plug.

7. The method of claim 3, wherein the occlusal plug contact area is harder than the occlusal surface of the appliance.

8. The method of claim 3, wehrein the occlusal plug contact area is softer than the teeth coming in contact with the occlusal surface.

9. An improved dental appliance having an occlusal surface wherein the improvement comprises a preformed wear resistant cylindrical dumbbell shaped occlusal plug embedded in the appliance through an occlusal contact area, one end of the plug serving as a means for anchoring the plug in the appliance, and the other end of the plug serving as the occlusal contact area.

10. An improved temporomandibular joint appliance having an occlusal surface wherein the improvement comprises a preformed wear resistant cylindrical dumbbell shaped occlusal plug embedded in the appliance through an occlusal contact area, one end of the plug serving as a means for anchoring the plug in the appliance, and the other end of the plug serving as the occlusal contact area.

11. An improved mandibular orthopedic repositioning appliance having an occlusal surface wherein the improvement comprises a preformed wear resistant cylindrical dumbbell shaped occlusal plug embedded in the appliance through an occlusal contact area, one end of the plug serving as a means for anchoring the plug in the appliance, and the other end of the plug serving as the occlusal contact area.

12. The improved dental appliance of claim 11, wherein a major portion of the appliance is made of an acrylic resin in which the occlusal plug is embedded.

13. The improved appliance of claim 11, wherein the one end of the plug serving as the anchoring end has a securing means for preventing rotation of the plug.

14. The improved appliance of claim 13, wherein the securing means is a notch in the anchoring end of the plug.

15. The improved appliance of claim 11 wherein the occlusal plug contact area is harder than the occlusal surface of the appliance.

16. The improved appliance of claim 11, wherein the occlusal plug contact area is softer than the teeth coming in contact with the occlusal surface.

17. A method of embedding an occlusal plug in an acrylic dental appliance having an occlusal surface comprising:
(a) locating an occlusal contact area on the occlusal surface;
(b) preparing an opening at the occlusal contact area for the plug;
(c) filling the opening with an acrylic resin;
(d) pressing the occlusal plug in the filled opening;
(e) inserting the appliance in the patients mouth;
(f) closing the patients mouth to properly seat the occlusal plug; and
(g) curing the acrylic.

18. The method of claim 17 wherein the dental appliance is a temporomandibular joint appliance.

19. The method of claim 17 wherein the dental appliance is mandibular orthopedic repositioning appliance.

* * * * *